(12) United States Patent
Wiesmueller et al.

(10) Patent No.: US 8,513,456 B2
(45) Date of Patent: Aug. 20, 2013

(54) METHOD FOR PRODUCING A CARNOSIC ACID-RICH PLANT EXTRACT

(75) Inventors: Johann Wiesmueller, Garching (DE); Franz Michlbauer, Kirchweidach (DE); Ralf Kahleyss, St. Georgen (DE); Helmut Hausner, Trostberg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/503,653

(22) PCT Filed: Oct. 12, 2010

(86) PCT No.: PCT/EP2010/065268
§ 371 (c)(1),
(2), (4) Date: Apr. 23, 2012

(87) PCT Pub. No.: WO2011/054631
PCT Pub. Date: May 12, 2011

(65) Prior Publication Data
US 2012/0209026 A1    Aug. 16, 2012

(30) Foreign Application Priority Data

Oct. 26, 2009  (DE) .......................... 10 2009 045 994

(51) Int. Cl.
*C07C 61/08* (2006.01)
(52) U.S. Cl.
USPC ...................................................... 562/466
(58) Field of Classification Search
CPC ...................................................... C07C 51/47
See application file for complete search history.

(56) References Cited

U.S. PATENT DOCUMENTS 4,584,140 A * 4/1986 Blewett et al. ................ 554/176
5,256,700 A * 10/1993 Aeschbach et al. ........... 514/732

FOREIGN PATENT DOCUMENTS

| CN | 1333326 A | 1/2002 |
| CN | 1417286 A | 5/2003 |
| DE | 43 06 303 A1 | 9/1994 |
| EP | 0 454 097 A1 | 4/1991 |
| EP | 0454097 A1 * | 10/1991 |

OTHER PUBLICATIONS

Diaz-Reinoso et al, Agricultural and Food Chemistry, Supercritical CO2 Extraction and Purification of Compounds with Antioxidant Activity, 2006, 54, pp. 2441-2469.*
Kubiak et al, Kubiak Research Group, UCSD, 2008, retrieved from http://kubiak.ucsd.edu/manual/filtration.php Jan. 9, 2013.*
English translation of International Search Report for PCT/EP2010/065268 filed Oct. 12, 2010.
English translation of the Written Opinion of the International Searching Authority for PCT/EP2010/065268 filed Oct. 12, 2010.
English language translation of Letter 1 from Applicant to EPO.
English language translation of Letter 2 from Applicant to EPO.
English language translation of the International Preliminary Examination Report for PCT/EP2010/065268 filed Oct. 12, 2010.
$1^{st}$ English language abstract for DE 43 06 303, listed as document B1 above.
$2^{nd}$ English language abstract for DE 43 06 303, listed as document B1 above.
English language abstract for CN 1333326 A, listed as document B3 above.
English language abstract for CN 1417286 A, listed as document B4 above.
English language translation of Office Action with attached Search Report for corresponding Chinese application 201080048633.X.

* cited by examiner

Primary Examiner — Paul A Zucker
(74) Attorney, Agent, or Firm — Law Office of: Michael A. Sanzo, LLC

(57) ABSTRACT

A carnosic acid-rich plant extract can be produced by extracting a dried and comminuted plant material containing carnosic acid with supercritical $CO_2$ at a pressure of at least 200 bar and at a temperature of at most 100° C. In a first step, supercritical $CO_2$ in a quantity of 10 to 50 kg of $CO_2$ per kg of plant material is passed through the plant material to obtain a first $CO_2$ extract. In a second step, additional supercritical $CO_2$ is passed through the plant material to obtain a second $CO_2$ extract, and a carnosic acid-rich plant extract is separated from the second $CO_2$ extract by lowering the pressure.

20 Claims, No Drawings

METHOD FOR PRODUCING A CARNOSIC ACID-RICH PLANT EXTRACT

CROSS REFERENCE TO RELATED APPLICATIONS

The present application is US national stage of international application, PCT/EP2010/065268 which had an international filing date of Oct. 12, 2010, and which was published in German under PCT Article 21(2) on May 12, 2011. Priority is claimed to German application DE 10 2009 045 994.4, filed on Oct. 26, 2009.

The invention is directed to a method for producing a carnosic acid-rich plant extract by extracting a carnosic acid-containing plant material with supercritical $CO_2$.

Carnosic acid is a plant ingredient which can be used in foods or cosmetics as a natural antioxidant instead of the antioxidants butylhydroxyanisol (BHA) and butylhydroxytoluene (BHT) often used hitherto. For such a use, carnosic acid-rich plant extracts are required which have a low intrinsic color and a low content of odor- and taste-imparting substances and which should contain as little solvent as possible.

EP 454 097 discloses methods for producing carnosic acid-rich extracts with a low content of essential oils from rosemary or sage. For this, either a two-stage extraction with supercritical $CO_2$ at firstly 300 to 350 bar and 35 to 40° C. and then 500 bar and 40° C. is carried out, or extraction at 500 bar and 40° C. with supercritical $CO_2$ is carried out and, from the resulting $CO_2$ extract, one extract at a time is precipitated fractionally in two pressure stages at firstly 115 to 120 bar and 75 to 85° C. and then 33 to 35 bar and 10 to 17° C. The method produces extracts with a content of carnosic acid of more than 25% by weight, although they are still greenish-brown in color. The method has the disadvantage that it is necessary to work at different pressure stages and that during a separation in two pressure stages the viscous extract obtained in the first pressure stage is poorly separable from the still supercritical $CO_2$-rich phase.

DE 43 06 303 discloses methods for obtaining plant oils by extraction with supercritical $CO_2$, in which the $CO_2$ extract is passed under supercritical conditions over a bed of bleaching earth in order to remove colorings.

The invention provides a method for producing a carnosic acid-rich plant extract which involves an extraction of a dried and comminuted carnosic acid-containing plant material with supercritical $CO_2$ at a pressure of at least 200 bar and a temperature of at most 100° C. During this extraction, in a first step, supercritical $CO_2$ is passed through the plant material in an amount of 10 to 50 kg of $CO_2$ per kg of plant material, giving a first $CO_2$ extract, in a second step, further supercritical $CO_2$ is passed through the plant material, giving a second $CO_2$ extract, and a carnosic acid-rich plant extract is precipitated from the second $CO_2$ extract by lowering the pressure.

The method according to the invention produces a plant extract with a high content of carnosic acid and does not have the disadvantages of the method known from EP 454 097.

In the method according to the invention, a dried and comminuted carnosic acid-containing plant material is extracted. Preferably, a plant material is used which is dried to a water content of less than 10% by weight. All drying methods known from the prior art can be used for drying the plant material. Preferably, the drying takes place at temperatures of less than 100° C., particularly preferably at less than 85° C. The plant material is preferably dried in uncomminuted form and/or with the exclusion of atmospheric oxygen in order to avoid a reaction of carnosic acid present therein with atmospheric oxygen during the drying. The plant material is used in comminuted form for the extraction. Preferably, the plant material is comminuted to a weight-based average particle size of less than 1.5 mm. All comminution methods known from the prior art can be used to comminute the plant material. Preferably, the comminution takes place at temperatures of less than 40° C. The plant material is preferably comminuted with the exclusion of atmospheric oxygen in order to avoid a reaction of carnosic acid present therein with atmospheric oxygen during the comminution.

Suitable carnosic acid-containing plant materials are plant parts of plants from the family of the Labiatae, preferably plant parts of plants of the genera *Rosmarinum* and *Salvia*. The plant material particularly preferably comprises leaves of rosemary (*Rosmarinum officinalis*) or sage (*Salvia officinalis*).

The dried and comminuted carnosic acid-containing plant material is extracted in the method according to the invention with supercritical $CO_2$ at a pressure of at least 200 bar and a temperature of at most 100° C. The temperature during the extraction must be more than 31° C. so that the $CO_2$ is in the supercritical state. Preference is given to extracting at a pressure of 280 to 1000 bar and particularly preferably at a pressure of 280 to 420 bar.

Suitable autoclaves for an extraction with supercritical $CO_2$ are known to the person skilled in the art from the prior art. Preferably, for the extraction, supercritical $CO_2$ is passed through a layer of carnosic acid-containing plant material. The supercritical $CO_2$ here can be passed through the layer of plant material either in up-flow or down-flow. The $CO_2$ here can be used either in pure form or mixed with up to 10% by weight of an entrainer known from the prior art. The entrainers used are preferably aliphatic alcohols having up to four carbon atoms, alkanes having up to six carbon atoms and aliphatic ketones having up to five carbon atoms. However, extraction without entrainer is preferred.

In the method according to the invention, in a first step, the supercritical $CO_2$ is passed through the plant material in an amount of 10 to 50 kg of $CO_2$ per kg of plant material, giving a first $CO_2$ extract. In a second step, further supercritical $CO_2$ is then passed through the plant material, giving a second $CO_2$ extract. Preferably here, further 80 to 250 kg of $CO_2$ per kg of plant material are passed through the plant material. Preferably, in the second step, the supercritical $CO_2$ is passed through the plant material at the same pressure as in the first step. A carnosic acid-rich plant extract is then precipitated from the second $CO_2$ extract by lowering the pressure. An oil-rich plant extract can be precipitated from the first $CO_2$ extract by lowering the pressure. Preferably, when lowering the pressure, the end pressure and the end temperature are chosen such that the $CO_2$ changes from the supercritical state to the gaseous state. Suitable separators for precipitating the plant extract by lowering the pressure are known to the person skilled in the art from the prior art in respect of extractions with supercritical $CO_2$.

Compared with the isolation of a carnosic acid-rich plant extract by the two-stage lowering of the pressure known from EP 454 097, the method according to the invention has the advantage that a carnosic acid-rich plant extract with a smaller proportion of essential oils is obtained which has a reduced odor.

In a preferred embodiment of the method according to the invention, the second $CO_2$ extract is passed through a solid absorbent under supercritical conditions prior to precipitating the plant extract. Absorbents which can be used here are all absorbents with which colorings co-extracted from the plant material can be absorbed. Preferably, the absorbents used are activated carbon, bleaching earth (Fuller's earth), kieselguhr, silica gel or cellulose. As absorbent, particular preference is given to using a bleaching earth which consists of a calcium-containing bentonite or a calcium-containing montmorillonite. Suitable bleaching earths are available from Südchemie under the trade name Tonsil®. The absorbent can be used in powder form or preferably as granules. This embodiment can be used to produce decolored carnosic acid-rich plant extracts.

The $CO_2$ extract is preferably passed through the solid absorbent under the same pressure and temperature conditions as for the extraction. The extraction and the passing through the absorbent can take place in apparatuses separate from one another or in the same apparatus.

Preferably, the first $CO_2$ extract is also passed through the solid absorbent before the oil-rich plant extract is separated off by lowering the pressure in order to also obtain the oil-rich plant extract in decolored form. The first $CO_2$ extract and the second $CO_2$ extract can be passed here separately from one another through the same absorbent or through different absorbents. Preferably, however, the first $CO_2$ extract and the second $CO_2$ extract are passed in succession through the same solid absorbent.

In a particularly preferred embodiment, the carnosic acid-containing plant material and the absorption material are arranged in an autoclave in the form of superimposed layers and the supercritical $CO_2$ is passed firstly through the layer of plant material and then through the layer of absorption material. If the supercritical $CO_2$ is passed here through the layer of plant material in up-flow, a layer of absorption material is arranged above the layer of plant material. If the supercritical $CO_2$ is passed through the layer of plant material in down-flow, a layer of absorption material is arranged underneath the layer of plant material. This embodiment has the advantage that a decolored carnosic acid-rich plant extract can be obtained in an extraction plant known from the prior art for extraction with supercritical $CO_2$ without further purification equipment or purification steps.

The example below illustrates the invention without, however, limiting the subject matter of the invention.

EXAMPLE 1 kg of rosemary needles dried to a water content of 8% by weight and ground to an average particle size of less than 1.5 mm are placed in the extraction container of an extraction autoclave. A layer of 100 g of Tonsil® Optimum 210 FF bleaching earth is applied onto the bed of ground rosemary needles. Supercritical $CO_2$ is then passed in up-flow through the bed at a pressure of 280 bar and a temperature of 65° C. The $CO_2$ extract obtained is initially fed to a first separator in which a first plant extract is precipitated at a pressure of 45 bar and a temperature of 35° C. After 30 kg of supercritical $CO_2$ had been passed through the bed, the $CO_2$ extract obtained was fed to a second separator in which a second plant extract was precipitated at a pressure of 45 bar and a temperature of 35° C. In total, 100 kg of supercritical $CO_2$ were passed through the bed. In the first separator, 77 g of an aqueous phase and 113 g of an orange-colored liquid plant extract were obtained which comprised 13% by weight of carnosic acid and 32% by weight of essential oil. In the second separator, 48 g of a yellow viscous plant extract were obtained which comprised 41% by weight of carnosic acid and less than 1% by weight of essential oil.

The invention claimed is:

1. A method for producing a carnosic acid-rich plant extract by extraction of a dried and comminuted carnosic acid-containing plant material with supercritical $CO_2$ at a pressure of at least 200 bar and a temperature of at most 100° C., said method comprising the steps of:
   a) in a first step, passing supercritical $CO_2$ through plant material in an amount of 10 to 50 kg of $CO_2$ per kg of plant material to give a first $CO_2$ extract;
   b) in a second step, passing further supercritical $CO_2$ through the plant material at the same pressure as in step a) to give a second $CO_2$ extract; and
   c) precipitating a carnosic acid-rich plant extract from the second $CO_2$ extract by lowering the pressure.

2. The method of claim 1, wherein the plant material comprises leaves of *Rosmarinum officinalis* or *Salvia officinalis*.

3. The method of claim 1, wherein extraction is carried out at a pressure of 280 to 1000 bar.

4. The method of claim 1, wherein, in the second step, $CO_2$ is passed through the plant material in an amount of from 80 to 250 kg per kg of plant material.

5. The method of claim 1, wherein an oil-rich plant extract is precipitated from the first $CO_2$ extract by lowering the pressure.

6. The method of claim 2, wherein extraction is carried out at a pressure of 280 to 1000 bar.

7. The method of claim 6, wherein, in the second step, $CO_2$ is passed through the plant material in an amount of from 80 to 250 kg per kg of plant material.

8. The method of claim 7, wherein an oil-rich plant extract is precipitated from the first $CO_2$ extract by lowering the pressure.

9. The method of claim 1, wherein the second $CO_2$ extract is passed through a solid absorbent under supercritical conditions prior to precipitating the plant extract.

10. The method of claim 9, wherein the first $CO_2$ extract and the second $CO_2$ extract are passed in succession through said solid absorbent.

11. The method of claim 9, wherein the absorbent is selected from the group consisting of activated carbon, bleaching earth, kieselguhr, silica gel and cellulose.

12. The method of claim 9, wherein the absorbent is a bleaching earth selected from the group consisting of calcium-containing bentonites and calcium-containing montmorillonites.

13. The method of claim 9, wherein the absorbent is used in the form of granules.

14. The method of claim 9, wherein the plant material and the absorption material are arranged in an autoclave in the form of superimposed layers and the supercritical $CO_2$ is passed first through a layer of plant material and then through a layer of absorption material.

15. The method of claim 9, wherein the plant material comprises leaves of *Rosmarinum officinalis* or *Salvia officinalis*.

16. The method of claim 15, wherein the first $CO_2$ extract and the second $CO_2$ extract are passed in succession through said solid absorbent.

17. The method of claim 16, wherein the absorbent is selected from the group consisting of activated carbon, bleaching earth, kieselguhr, silica gel and cellulose.

18. The method of claim 16, wherein the absorbent is a bleaching earth selected from the group consisting of calcium-containing bentonites and calcium-containing montmorillonites.

19. The method of claim 18, wherein the absorbent is used in the form of granules.

20. The method of claim 18, wherein the plant material and the absorption material are arranged in an autoclave in the form of superimposed layers and the supercritical $CO_2$ is passed first through a layer of plant material and then through a layer of absorption material.

\* \* \* \* \*